United States Patent
Yang et al.

(10) Patent No.: US 8,226,596 B2
(45) Date of Patent: Jul. 24, 2012

(54) BLOOD FLOW CONTROL SYSTEM, TENSION ADJUSTABLE INSTRUMENT AND METHOD THEREOF

(75) Inventors: Chung-Shi Yang, Taichung (TW); Leu-Wei Lo, Sindian (TW)

(73) Assignee: National Health Research Institutes, Miaoli County (TW)

( * ) Notice: Subject to any disclaimer, the term of this patent is extended or adjusted under 35 U.S.C. 154(b) by 1028 days.

(21) Appl. No.: 12/219,973

(22) Filed: Jul. 31, 2008

(65) Prior Publication Data

US 2009/0043251 A1  Feb. 12, 2009

Related U.S. Application Data

(60) Provisional application No. 60/954,423, filed on Aug. 7, 2007.

(51) Int. Cl.
*A61M 3/00* (2006.01)
(52) U.S. Cl. .................................................. 604/66
(58) Field of Classification Search ............... 604/8, 65, 604/66, 500; 606/151, 157, 158; 600/486, 600/505, 201–204
See application file for complete search history.

(56) References Cited

U.S. PATENT DOCUMENTS

| | | |
|---|---|---|
| 3,079,608 A | 3/1963 | Babkin |
| 4,646,740 A | 3/1987 | Peters et al. |
| 4,709,690 A * | 12/1987 | Haber ............................ 600/31 |
| 6,616,624 B1 * | 9/2003 | Kieval ............................ 604/8 |
| 2004/0006284 A1 | 1/2004 | Sayet et al. |

FOREIGN PATENT DOCUMENTS

| | | |
|---|---|---|
| TW | 200533318 | 10/2005 |
| TW | 200724181 | 7/2007 |

OTHER PUBLICATIONS

Taiwanese Office Action dated Jun. 28, 2011 for 097126701, which is a corresponding Taiwanese application, that cites TW 200724181A, US 6616624, TW 200533318A, US 3079608, and US 4646740.
Taiwanese Office Action dated Oct. 26, 2011 for 097126701, which is a corresponding Taiwanese application, that cites TW200724181, US6616624, US3079608, US2004/0006284, and Webster J.G., "Medical Instrumentation Application and Design", John Wiley & Sons Inc., 3rd ed., 1998, pp. 460-462.
John G. Webster et al., Medical Instrumentation Application and Design, John Wiley & Sons Inc., 3rd ed., 1998, pp. 460-462.

* cited by examiner

*Primary Examiner* — Christopher D Koharski
(74) *Attorney, Agent, or Firm* — WPAT, P.C.; Anthony King

(57) ABSTRACT

A blood flow control system, tension adjustable instrument and a method are disclosed. The blood flow control system comprises a detecting unit, a computing and a tension adjustable instrument. The detecting unit real-time monitors the biomolecular response condition of a living organ, and the computing unit dynamically controls the tension adjustable instrument to adjust the tension of the blood vessel based on the detecting result. Therefore the blood flow control system can maintain the biomolecular response condition over a predetermined range to reduce the risk of the liver organ being damaged and augment the curability.

7 Claims, 5 Drawing Sheets

BLOOD FLOW CONTROL SYSTEM, TENSION ADJUSTABLE INSTRUMENT AND METHOD THEREOF

REFERENCE TO RELATED APPLICATION

This Patent Application is based on Provisional Patent Application Ser. No. 60/954,423, filed 7 Aug. 2007, currently pending.

FIELD OF THE INVENTION

The present invention relates to a blood flow control system, a tension adjustable instrument and method thereof, and more particularly to a blood flow control system that keeps the biomolecular response condition over a predetermined range in terms of a tension-adjustable instrument with automatic feedback control.

BACKGROUND OF THE INVENTION

As is well known, hepatoma currently affects a significant number of people, particularly in Asian. In recent years, it has been drawing attention in North America and Europe as well. In recognition of the prevailing morbidity and mortality of hepatoma, improvement of the curative rate of hepatoma has been prominent its own necessity and immediateness. Among all the surgical means for hepatoma, the temporary hepatic artery occlusion is one of the most adopted treatments practiced by surgeon. Nevertheless, there is still a considerable risk of the liver being damaged so much as to cause death. What is need is a system or method to reduce the surgical risk and augment the curability.

In view of the shortcomings of the prior art, the inventor of the present invention based on years of experience to conduct experiments and modifications, and finally developed a blood flow control system, tension adjustable instrument and method thereof as a platform to better increase the therapeutic efficacy of temporary hepatic artery occlusion with minimal damage on normal tissue. It should be noted that this claimed system can be applied not only on the hepatic artery occlusion, but also for a spectrum of surgical process that involves ischemia such as organ transplantation, traditional cardiopulmonary bypass, and tumor enucleation.

SUMMARY OF THE INVENTION

The primary objective of the present invention is to provide a blood flow control system, tension adjustable instrument and method thereof to reduce the risk of the liver being damaged during artery occlusion.

A blood flow control system in accordance with the present invention comprises a detecting unit, a computing unit and a tension adjustable instrument. The detecting unit is for detecting a biomolecular response condition of a living organ. The computing unit is for calculating a control signal based on the detecting result of said detecting unit. The tension adjustable instrument is for clamping/unclamping a blood vessel of said living organ to control the amount of blood flowing into said living organ based on said control signal.

Preferably, the biomolecular response condition includes a blood oxygen (omitted) oxygenation condition in response to ischemia and/or reperfusion.

Preferably, the biomolecular response condition includes a blood glucose condition in response to ischemia and/or reperfusion.

Preferably, the computing unit uses a feedback control algorithm and at least one threshold to calculate a compensation data, and outputs the signal corresponding to the compensation data to the tension adjustable instrument for maintaining the biomolecular response condition over a predetermined range.

An embodiment of a tension adjustable instrument in accordance with the present invention comprises a jaw part, a push member and a driving unit coupled to the push member. The jaw part and the push member are used to clamp/unclamp a blood vessel. The driving unit is used to receive a control signal and drive the push member to move for adjusting the tension of the blood vessel based on the control signal.

Preferably, the tension adjustable instrument further comprises an elastomer mounted on said jaw part.

Preferably, the driving unit includes a motor, a hydraulic pressure driver or an air pressure driver.

Another embodiment of a tension adjustable instrument in accordance with the present invention comprises a pair of jaw parts, a push member and a driving unit coupled to the push member. Each of the jaw parts having a first portion and a second portion, the first portions of said jaw parts are used to clamp/unclamp a blood vessel and the distance between the first portions of the jaw parts is related to the movement of the second portions of the jaw parts. The push member is used to push the second portions of the jaw parts. The driving unit is used to receive a control signal and drive the push member to move for adjusting the tension of the blood vessel based on the control signal.

Preferably, the driving unit includes a motor, a hydraulic pressure driver or an air pressure driver.

Further, the invention provides a method for controlling a biomolecular response condition of a living organ. The method comprises the steps of: using a tension adjustable instrument to clamp/unclamp a blood vessel of the living organ; detecting the biomolecular response condition of the living organ; generating a control signal based on the detecting result; controlling the tension adjustable instrument to adjust the tension of the blood vessel to control the amount of blood flowing into the living organ based on the control signal.

Preferably, the biomolecular response condition includes a blood oxygen (omitted) oxygenation condition in response to ischemia and/or reperfusion.

Preferably, the biomolecular response condition includes a blood glucose condition in response to ischemia and/or reperfusion.

Preferably, the control signal corresponds to a compensation data calculated by using a feedback control algorithm and at least one threshold.

To make it easier for our examiner to understand the objective of the invention, its structure, innovative features, and performance, we use preferred embodiments together with the attached drawings for the detailed description of the invention.

BRIEF DESCRIPTION OF THE DRAWINGS

The subject matter regarded as the invention is particularly pointed out and distinctly claimed in the concluding portion of the specification. The invention, both as to system and method of operation, together with features and advantages thereof may best be understood by reference to the following detailed description with the accompanying drawings in which:

DETAILED DESCRIPTION OF THE PREFERRED EMBODIMENTS

The present invention relates to a blood flow control system, a tension adjustable instrument and method thereof. While the specifications describe at least one embodiment of the invention considered best modes of practicing the invention, it should be understood that the invention can be implemented in many ways and is not limited to the particular examples described below or to the particular manner in which any features of such examples are implemented.

Figure 1:
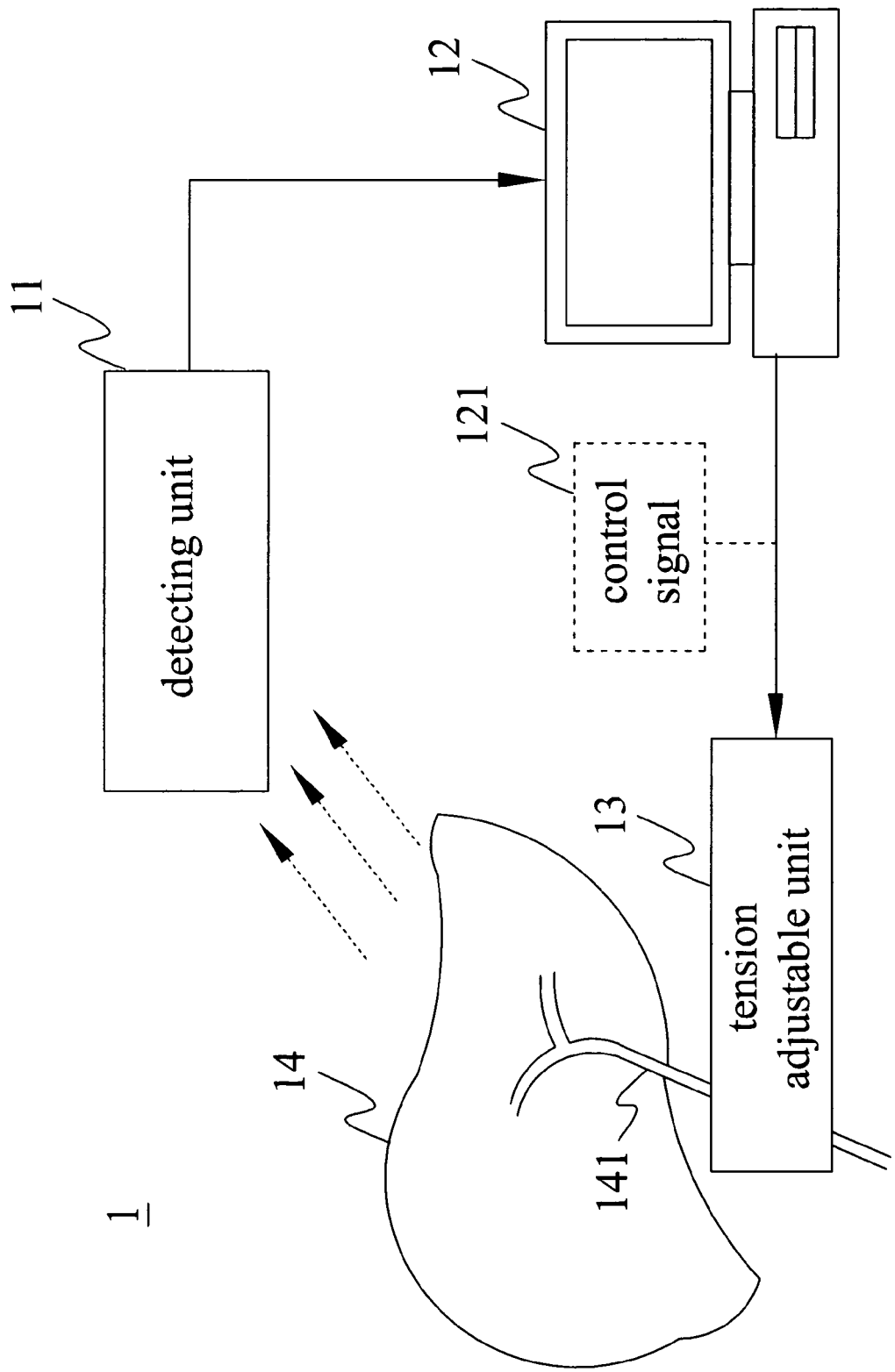
FIG. 1 is a block diagram of a blood flow control system in accordance with the present invention.

FIG. 1 illustrates a schematic view of a blood flow control system in accordance with the present invention. A blood flow control system 1 comprises a detecting unit 11, a computing unit 12 and a tension adjustable instrument 13. The detecting unit 11 is used to detect a biomolecular response of a living organ 14. Preferably, the biomolecular response condition includes the blood oxygenation condition, the blood glucose condition, the gene regulation condition, the ion concentration condition, the metabolite balance condition, the protein activated/deactivated functional change in response to ischemia and/or reperfusion. Preferably, the detecting unit 11 can comprise a phosphorometer, a camera and an image processing apparatus. The phosphorometer and the camera are used to capture an oxygen-dependent phosphorescence quenching image of tissue of the living organ 14, and image analysis apparatus can analyze this image to determine the ischemic condition, i.e. tissue oxygenation, of a living organ 14. Besides, the detecting unit 11 also can be a NIR oxygen measuring apparatus, or the detecting unit 11 can be a luciferase and s-Galactosidase reporter gene assay system for measuring the gene regulations condition, or a bioluminescence imaging system or any other molecular imaging modalities targeting on imaging of gene expression/regulation in vivo.

The computing unit 12 is used to calculate a compensation data based on a feedback control algorithm and at least one predetermined threshold, then the computing unit 12 outputs a control signal corresponding to the compensation data to the tension adjustable instrument 13. The tension adjustable instrument 13 is used to clamp/unclamp a blood vessel 141 of the living organ 14 to control the amount of blood flowing into the living organ 14 based on the control signal 121.

If the tension of the blood vessel 141 is too great and the reduction of amount of blood flowing into the living organ 14 makes the blood oxygen or the blood glucose detected by the detecting unit 11 lower than the predetermined threshold, the computing unit 12 will generate the control signal 121 to drive the tension adjustable instrument 13 to loose the blood vessel 141 in an appropriate degree for increasing the blood oxygen or the blood glucose and prevent the living organ 14 from being damaged. In the other hand, if the blood oxygen or the blood glucose detected by the detecting unit 11 higher than the predetermined threshold, the computing unit 12 will drive the tension adjustable instrument 13 to tighten the blood vessel 141 for decreasing the blood oxygen or the blood glucose.

Figure 2:
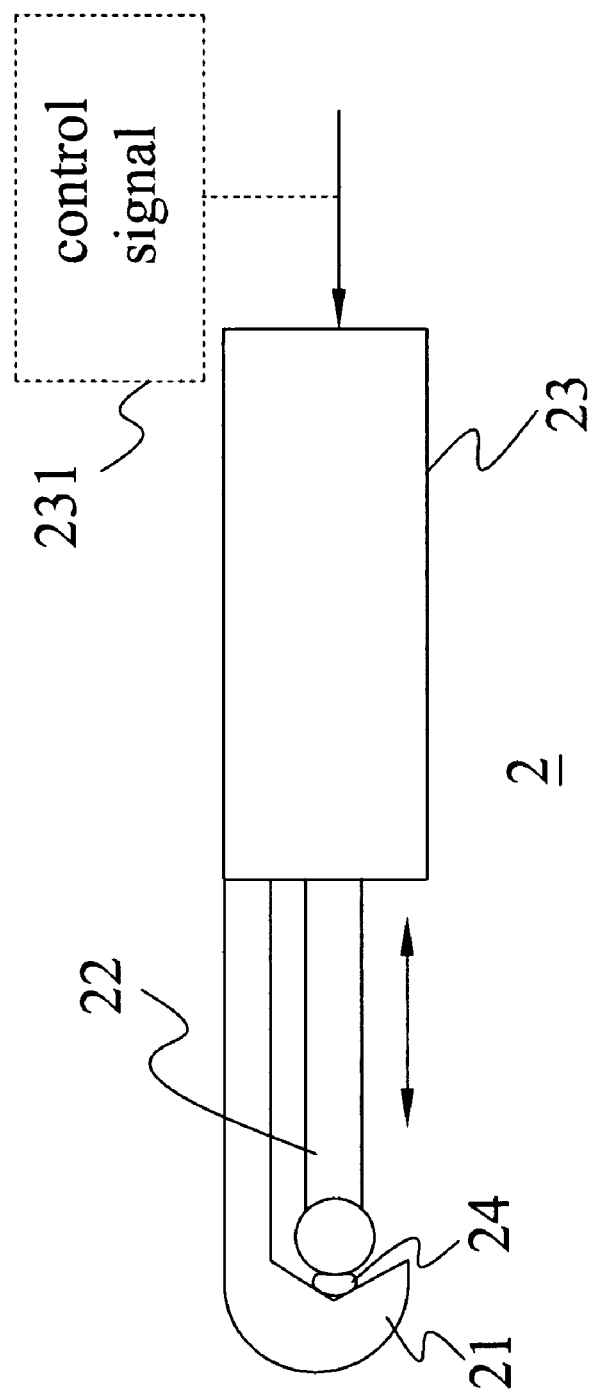
FIG. 2 is a schematic view of experiment results of implementing a Doppler experiment platform as a blood flow control system in accordance with the present invention.
Figure 5:
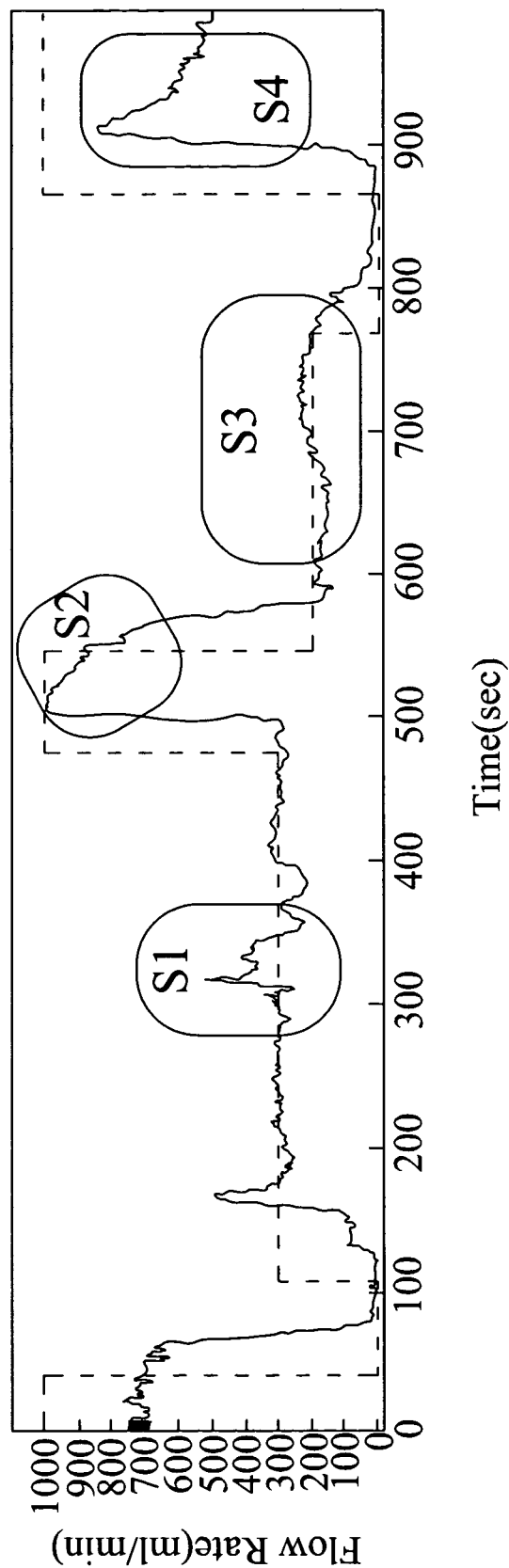
FIG. 5 is a flow chart of an embodiment of a method for controlling a biomolecular response condition in accordance with the present invention.

FIG. 2 illustrates a schematic view of experimental results of implementing a Doppler experimental platform as a blood flow control system in accordance with the present invention. The Doppler experimental platform measures a flow rate by a Laser Doppler Velocimetry to output as a feedback signal, and accordingly to adjust the tension of a blood vessel by a tension adjustable instrument to control the amount of blood flow. As shown in FIG. 5, the bold line is a real flow rate data, and the broken line is a designated flow rate.

Section S1 represents a pulse resulting from adding liquid. Section S2 represents delays resulting from transmitting a control signal. However the blood flow control system makes the flow rate return to the designate value efficiently, as shown in section 1 and section 2 in FIG. 2.

Section S3 represents the condition of the flow rate returning to the designate value gradually, while the tension to the blood vessel corresponds to the control signal. Section S4 represents a pulse resulting from reducing the tension to the blood vessel suddenly. However after several tens seconds, the floe rate returns to the designate value, as shown in section 3 and section 4 in FIG. 2. By changing the designate flow rate in each phase and observing the experiment data, the reliability of the blood flow control system can be verified.

By real-time monitoring the biomolecular response of a living organ 14 and dynamically modulating the tension of the blood vessel 141, the blood flow control system 1 can maintain the biomolecular response condition over a predetermined range to reduce the risk of the liver organ 14 being damaged and augment the curability.

Figure 3:
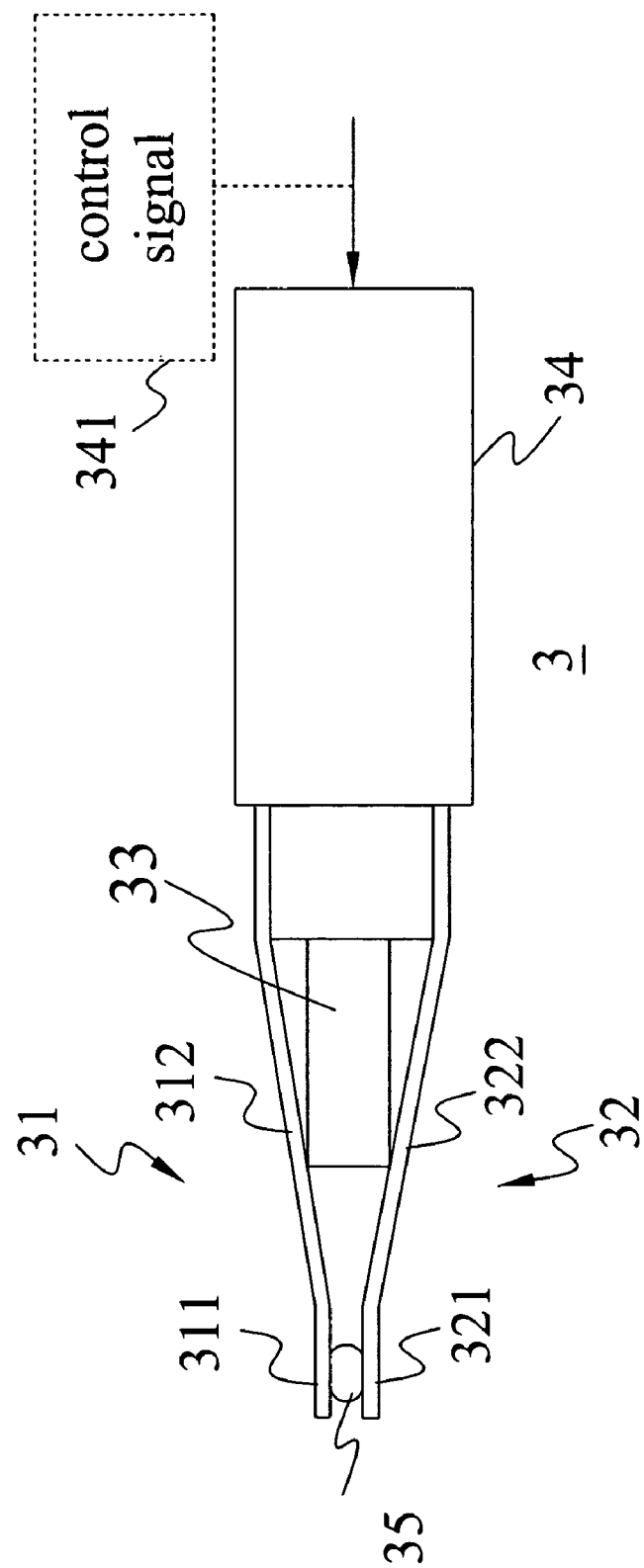
FIG. 3 is a schematic view of an embodiment of a tension adjustable instrument in accordance with the present invention.

FIG. 3 illustrates a schematic view of an embodiment of a tension adjustable instrument in accordance with the present invention. The tension adjustable instrument 2 comprises a jaw part 21, a push member 22 and a driving unit 23 coupled to the push member 22. The jaw part 21 and a push member 22 are used to clamp/unclamp a blood vessel 24. The driving unit 23 receives a control signal 231 and drives the push member 22 to move forward for increasing the tension of the blood vessel 24, or move backward for decreasing the tension of the blood vessel 24. Preferably, the control signal 231 is a pulse width modulation signal. Furthermore, the tension adjustable instrument 2 can comprise an elastomer which is mounted on the jaw part 21. The elastomer can prevent the blood vessel 24 from being damaged in clipping. Preferably, the driving unit 23 is a motor, a hydraulic pressure driver or an air pressure driver.

Figure 4:
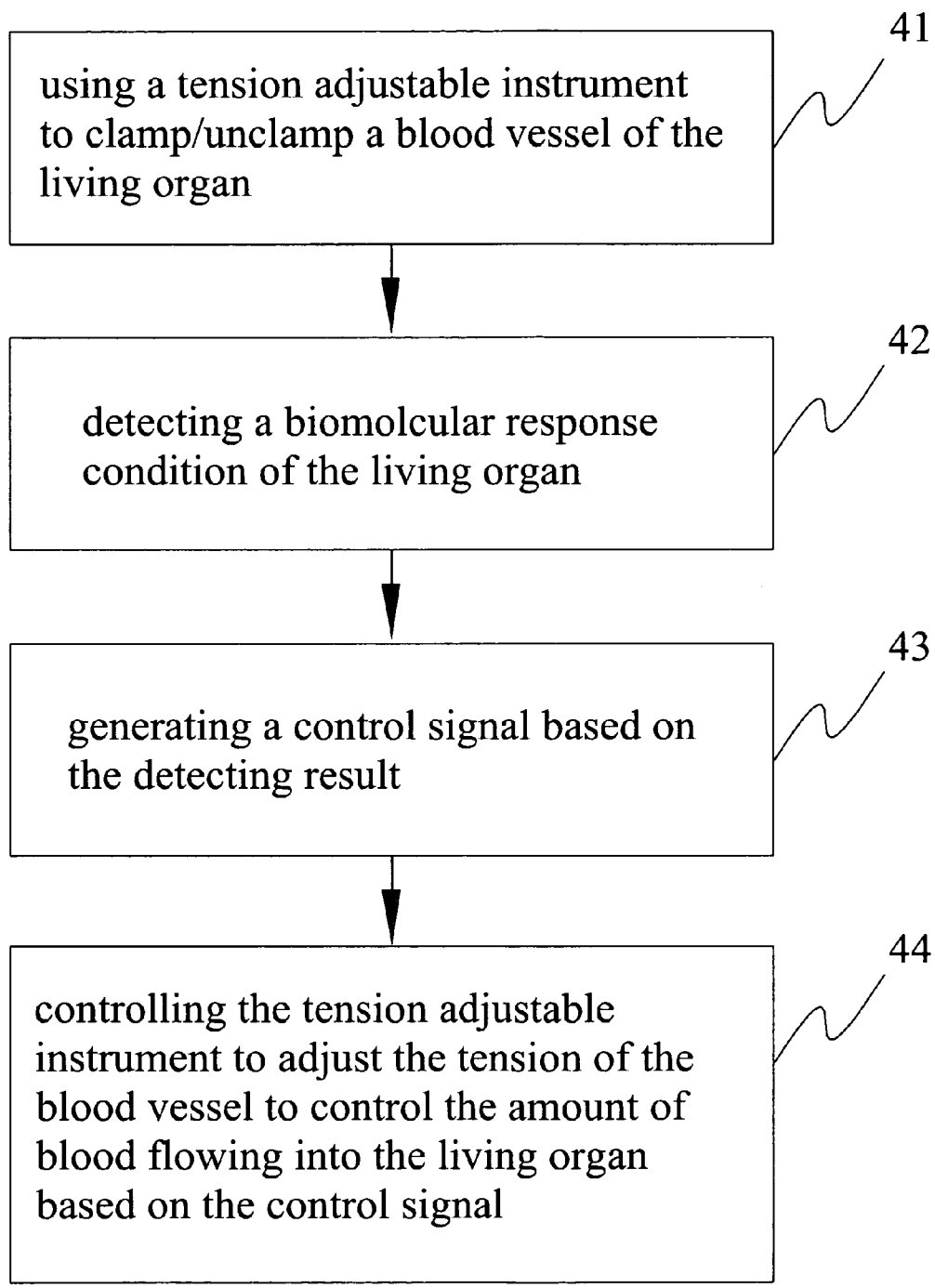
FIG. 4 is a schematic view of another embodiment of a tension adjustable instrument in accordance with the present invention.

FIG. 4 illustrates a schematic view of another embodiment of a tension adjustable instrument in accordance with the present invention. The tension adjustable instrument 3 comprises a first jaw part 31, a second jaw part 32, a push member 33 and a driving unit 34 coupled to the push member 33. The first jaw part 31 has a first portion 311 and a second portion 312. The second jaw part 32 has a first portion 321 and a second portion 322. The first portion 311 and the first portion 321 are used to clamp/unclamp a blood vessel 35. The driving unit 34 is used to receive a control signal 341 and drive the push member 33 to move forward or move backward based on the control signal 341. When moving forward, the push member 33 can push the second portion 312 and the second portion 322 to remove from each other, so the distance between the first portion 311 and the first portion 321 becomes larger and the tension of the blood vessel 35 decreases. In the other hand, when the push member 33 is driven to move backward, the second portion 312 and the second portion 322 can approach each other, so the distance between the first portion 311 and the first portion 321 becomes smaller and the tension of the blood vessel 35 increases. The control signal 341 can be a pulse width modulation signal. Preferably, the driving unit 34 is a motor, a hydraulic pressure driver or an air pressure driver.

FIG. 5 illustrates a flow chart of a method for controlling a biomolecular response condition of a living organ in accordance with the present invention. The method comprises the follow steps. In step 41, a tension adjustable instrument is used to clamp/unclamp a blood vessel of the living organ, for limiting the blood flowing into the living organ. In step 42, the biomolecular response condition of a living organ is detected. Preferably, the biomolecular response condition includes the blood oxygenation condition, the blood glucose condition, the gene regulation condition, the ion concentration condition, the metabolite balance condition, the protein activated/deactivated functional change in response to ischemia and/or reperfusion.

Besides, the operator can use a phosphorometer, a camera and an image processing apparatus for capturing an oxygen-dependent phosphorescence quenching image of tissue of the living organ and analyzing this image to determine the ischemic condition, i.e. tissue oxygenation, of a living organ; or use a NIR oxygen measuring apparatus for measuring the blood oxygenation condition; or use a luciferase and s-Galactosidase reporter gene assay system for measuring the gene regulations condition, or a bioluminescence imaging system or any other molecular imaging modalities targeting on imaging of gene expression/regulation in vivo.

In step 43, a control signal is generated based on the detecting result. The control signal 341 can be a pulse width modulation signal. In step 44 the tension adjustable instrument is controlled to adjust the tension of the blood vessel for controlling the amount of blood flowing into the living organ based on said control signal. In such feedback control scheme, when the biomolecular response condition is higher than a predetermined threshold, the tension adjustable instrument can be controlled to tighten the blood vessel. In the other hand, the tension adjustable instrument can be controlled to loose the blood vessel if the biomolecular response condition is lower than the predetermined threshold. Therefore, the biomolecular response condition can be maintained over a predetermined range.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. A tension adjustable instrument applicable to hepatic artery occlusion for determining ischemic condition of a liver organ, comprising:
   a hook-shaped jaw part and a push member, for clamping/unclamping a blood vessel of the liver organ, said hook-shaped jaw part having two faces facing said push member and a recess between said two faces; and
   a driving unit coupled to said push member, for receiving a control signal output from a detecting unit disposed near the liver organ and detecting oxygen condition of tissues of the liver organ, and driving said push member to move toward said recess for adjusting the tension of said blood vessel of the liver organ based on said control signal, wherein when the tension of said blood vessel of the liver organ is decreases, the oxygen condition of the tissues of the liver organ increases.

2. The tension adjustable instrument of claim 1, wherein further comprising an elastomer mounted on said hook-shaped jaw part.

3. The tension adjustable instrument of claim 1, wherein said control signal is a pulse width modulation signal.

4. The tension adjustable instrument of claim 1, wherein said driving unit includes a motor, a hydraulic pressure driver or an air pressure driver.

5. A tension adjustable instrument applicable to hepatic artery occlusion for determining ischemic condition of a liver organ, comprising:
   a pair of jaw parts, each of said jaw parts having a first portion and a second portion, said first portions of said jaw parts being in parallel each other and a distance between said second portions of said jaw parts gradually becoming larger, said first portion of said jaw parts pressing a blood vessel of the liver organ and the distance between said first portions of said jaw parts related to the movement of said second portions of said jaw parts;
   a push member disposed between said second portions of said jaw parts, for pushing said second portions of said jaw parts; and
   a driving unit coupled to said push member and connected with said second portions of said jaw parts, for receiving a control signal output from a detecting unit disposed near the liver organ and detecting oxygen condition of tissues of the liver organ, and driving said push member to move for adjusting the tension of said blood vessel of the liver organ based on said control signal;
   wherein when said push member is moved in a direction toward to said first portions, the distance between said first portions becomes larger and the tension of said blood vessel of the liver organ decreases, such that the oxygen condition of the tissues of the liver organ increases.

6. The tension adjustable instrument of claim 5, wherein said control signal is a pulse width modulation signal.

7. The tension adjustable instrument of claim 5, wherein said driving unit includes a motor, a hydraulic pressure driver or an air pressure driver.

* * * * *